(12) United States Patent
Aminy et al.

(10) Patent No.: US 9,066,601 B1
(45) Date of Patent: Jun. 30, 2015

(54) HEATING MATTRESS

(71) Applicants: Zamarud Aminy, Elk Grove, CA (US); Mohammad Aminy, Elk Grove, CA (US)

(72) Inventors: Zamarud Aminy, Elk Grove, CA (US); Mohammad Aminy, Elk Grove, CA (US)

( * ) Notice: Subject to any disclaimer, the term of this patent is extended or adjusted under 35 U.S.C. 154(b) by 88 days.

(21) Appl. No.: 13/888,618

(22) Filed: May 7, 2013

(51) Int. Cl.
*A47C 21/04* (2006.01)
*A61F 7/00* (2006.01)

(52) U.S. Cl.
CPC . *A47C 21/04* (2013.01); *A61F 7/00* (2013.01); *A47C 21/046* (2013.01); *A47C 21/044* (2013.01); *A47C 21/048* (2013.01); *A47C 21/042* (2013.01)

(58) Field of Classification Search
CPC .... A47C 21/04; A47C 21/046; A47C 21/044; A47C 21/048; A47C 21/042; A61F 7/00
USPC ............ 5/421, 690, 740, 726, 652.2
See application file for complete search history.

(56) References Cited

U.S. PATENT DOCUMENTS

| | | | |
|---|---|---|---|
| 3,529,310 A * | 9/1970 | Olmo | 5/423 |
| 4,162,393 A | 7/1979 | Balboni | |
| 4,423,308 A | 12/1983 | Callaway et al. | |
| 4,884,304 A * | 12/1989 | Elkins | 5/421 |
| 5,448,788 A * | 9/1995 | Wu | 5/421 |
| 5,555,579 A * | 9/1996 | Wu | 5/421 |
| D382,090 S | 8/1997 | Pruett | |
| 7,181,787 B2 | 2/2007 | Wu | |
| 2005/0278863 A1 * | 12/2005 | Bahash et al. | 5/726 |
| 2006/0162074 A1 * | 7/2006 | Bader | 5/421 |
| 2006/0191886 A1 | 8/2006 | Pak | |
| 2007/0257018 A1 | 11/2007 | Huang | |
| 2007/0272673 A1 | 11/2007 | Keane | |
| 2009/0078690 A1 | 3/2009 | Lee et al. | |
| 2011/0031230 A1 | 2/2011 | Kim | |
| 2011/0289683 A1 * | 12/2011 | Mikkelsen et al. | 5/421 |

* cited by examiner

*Primary Examiner* — Peter M Cuomo
*Assistant Examiner* — Brittany Wilson

(57) ABSTRACT

The heating and cooling mattress is a mattress for a bed that includes a heating member and a cooling member, which work to either heat or cool the mattress when in use. The heating member is constructed of a heating element that traverses along a first plane, and which evenly distributes heat along an entire surface area of the mattress. The cooling member is constructed of a refrigeration cycle from which a condensing line traverses along a second plane in order to cool down the mattress. The heating member and the cooling member are independent of one another, but work alternately such that either the cooling member or the heating member is only able to operate at a given time. The first plane for the heating member is located at a lower elevation with respect to the second plane for the cooling member.

13 Claims, 3 Drawing Sheets

HEATING MATTRESS

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of mattresses, more specifically, a mattress that is able to heat or cool itself.

B. Discussion of the Prior Art

As will be discussed immediately below, no prior art discloses a mattress for a bed that includes a heating member and a cooling member, which work to either heat or cool the mattress when in use; wherein the heating member is constructed of a heating element that traverses along a first plane, and which evenly distributes heat along an entire surface area of the mattress; wherein the cooling member is constructed of a refrigeration cycle from which a condensing line traverses along a second plane in order to cool down the mattress; wherein the heating member and the cooling member are independent of one member or the heating member is only able to operate at a given time; wherein the first plane for the heating member is located at a lower elevation with respect to the second plane for the cooling member; wherein a control member is located on a side surface of the mattress, and enables an end user to select a desired output of either the cooling member or the heating member; wherein an optional remote control can be used in lieu of the control member in order to provide remote operation of the cooling member and the heating member.

The Lee et al. Patent Application Publication (U.S. Pub. No. 2009/0078690) discloses a fiber reinforced heating unit and mattress. However, the mattress does not feature a heating member and a cooling member that work in order to heat up or cool down the mattress.

The Keane Patent Application Publication (U.S. Pub. No. 2007/0272673) discloses an electrically heated mattress and pad. Again, the mattress and pad does not include both a heating member and a cooling member that work in order to heat up or cool down the mattress.

The Huang Patent Application Publication (U.S. Pub. No. 2007/0257018) discloses a programmable thermally controlled heating mattress. Again, the mattress is only directed to heating up the mattress and does not include a cooling member that can cool down the mattress.

The Pak Patent Application Publication (U.S. Pub. No. 2006/0191886) discloses a heat mattress for a bed having springs and a heating wire that are electrically connected to an electric source for heating. Again, the mattress is only able to heat up the mattress, and unable to cool down via a cooling member.

The Kim Patent Application Publication (U.S. Pub. No. 2011/0031230) discloses a built-in heating device for a mattress. Again, the device is only able to heat up a mattress.

The Wu patent (U.S. Pat. No. 7,181,787) discloses an air mattress assembly having a heating device. Again, the mattress assembly is only able to heat up the mattress.

The Balboni patent (U.S. Pat. No. 4,162,393) discloses an electric heating mattress. Again, the mattress assembly is only able to heat up the mattress.

The Callaway et al. patent (U.S. Pat. No. 4,423,308) discloses a thermally controllable heating mattress. Again, the mattress assembly is only able to heat up the mattress.

The Electro Warmth Heated Mattress Pad, a non-patent piece of prior art, discloses a mattress that is able to warm itself.

While the above-described devices fulfill their respective and particular objects and requirements, they do not describe a mattress for a bed that includes a heating member and a cooling member, which work to either heat or cool the mattress when in use; wherein the heating member is constructed of a heating element that traverses along a first plane, and which evenly distributes heat along an entire surface area of the mattress; wherein the cooling member is constructed of a refrigeration cycle from which a condensing line traverses along a second plane in order to cool down the mattress; wherein the heating member and the cooling member are independent of one another, but work alternatively such that either the cooling member or the heating member is only able to operate at a given time; wherein the first plane for the heating member is located at a lower elevation with respect to the second plane for the cooling member; wherein a control member is located on a side surface of the mattress, and enables an end user to select a desired output of either the cooling member or the heating member; wherein an optional remote control can be used in lieu of the control member in order to provide remote operation of the cooling member and the heating member. In this regard, the heating and cooling mattress departs from the conventional concepts and designs of the prior art.

SUMMARY OF THE INVENTION

The heating and cooling mattress is a mattress for a bed that includes a heating member and a cooling member, which work to either heat or cool the mattress when in use. The heating member is constructed of a heating element that traverses along a first plane, and which evenly distributes heat along an entire surface area of the mattress. The cooling member is constructed of a refrigeration cycle from which a condensing line traverses along a second plane in order to cool down the mattress. The heating member and the cooling member are independent of one another, but work alternately such that either the cooling member or the heating member is only able to operate at a given time. The first plane for the heating member is located at a lower elevation with respect to the second plane for the cooling member. A control member is located on a side surface of the mattress, and enables an end user to select a desired output of either the cooling member or the heating member. An optional remote control can be used in lieu of the control member in order to provide remote operation of the cooling member and the heating member.

It is an object of the invention to provide a bed mattress that includes both a heating member and a cooling member such that the mattress is able to heat up or cool down at the discretion of the end user.

A further object of the invention is to provide a mattress wherein the cooling member operates alternately with respect to the cooling member so as to prevent counter-productive use of the two members.

A further object of the invention is to provide a first plane for the heating element of the heating member to be at a lower elevation with respect to the second plane for the condenser line of the cooling member so that the thermal efficacy is maintained.

These together with additional objects, features and advantages of the heating and cooling mattress will be readily apparent to those of ordinary skill in the art upon reading the following detailed description of presently preferred, but nonetheless illustrative, embodiments of the heating and cooling mattress when taken in conjunction with the accompanying drawings.

In this respect, before explaining the current embodiments of the heating and cooling mattress in detail, it is to be understood that the heating and cooling mattress is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the heating and cooling mattress.

It is therefore important that the claims be regarded as including such equivalent construction insofar as they do not depart from the spirit and scope of the heating and cooling mattress. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
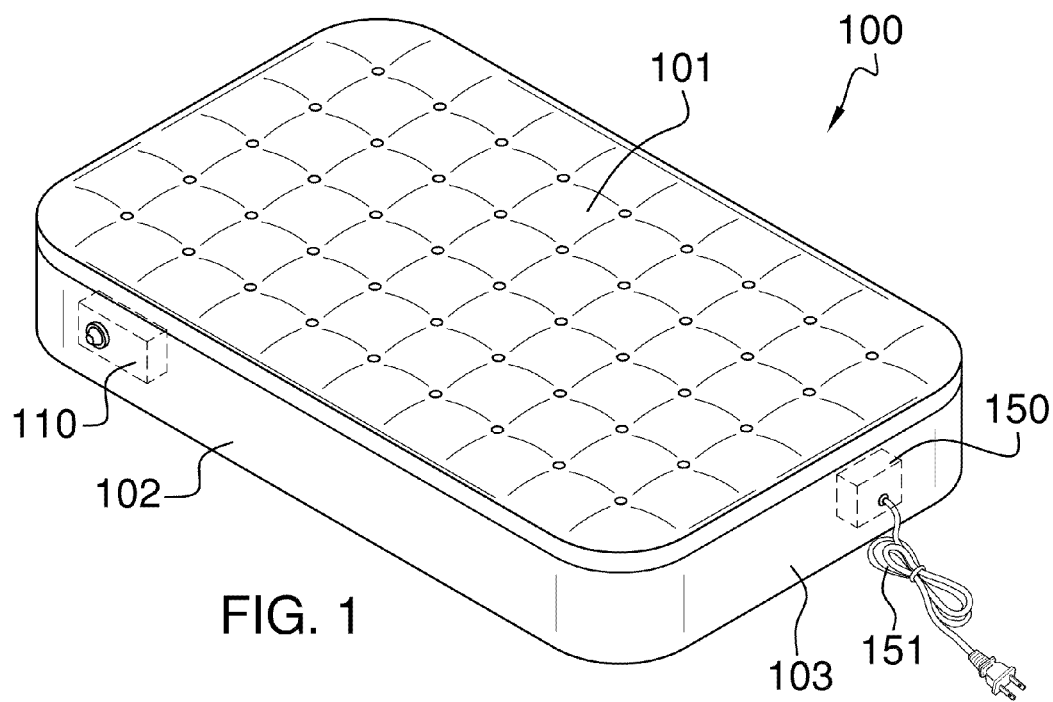
FIG. 1 illustrates a perspective view of the heating and cooling mattress by itself.
Figure 2:
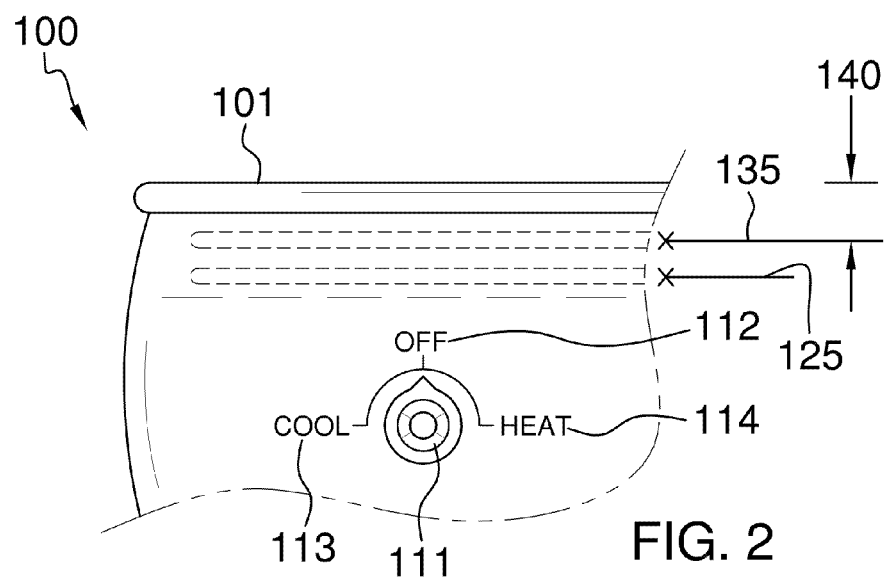
FIG. 2 illustrates a detailed side view of the control member on a side surface of the mattress and depicting the first and second planes.
Figure 3:
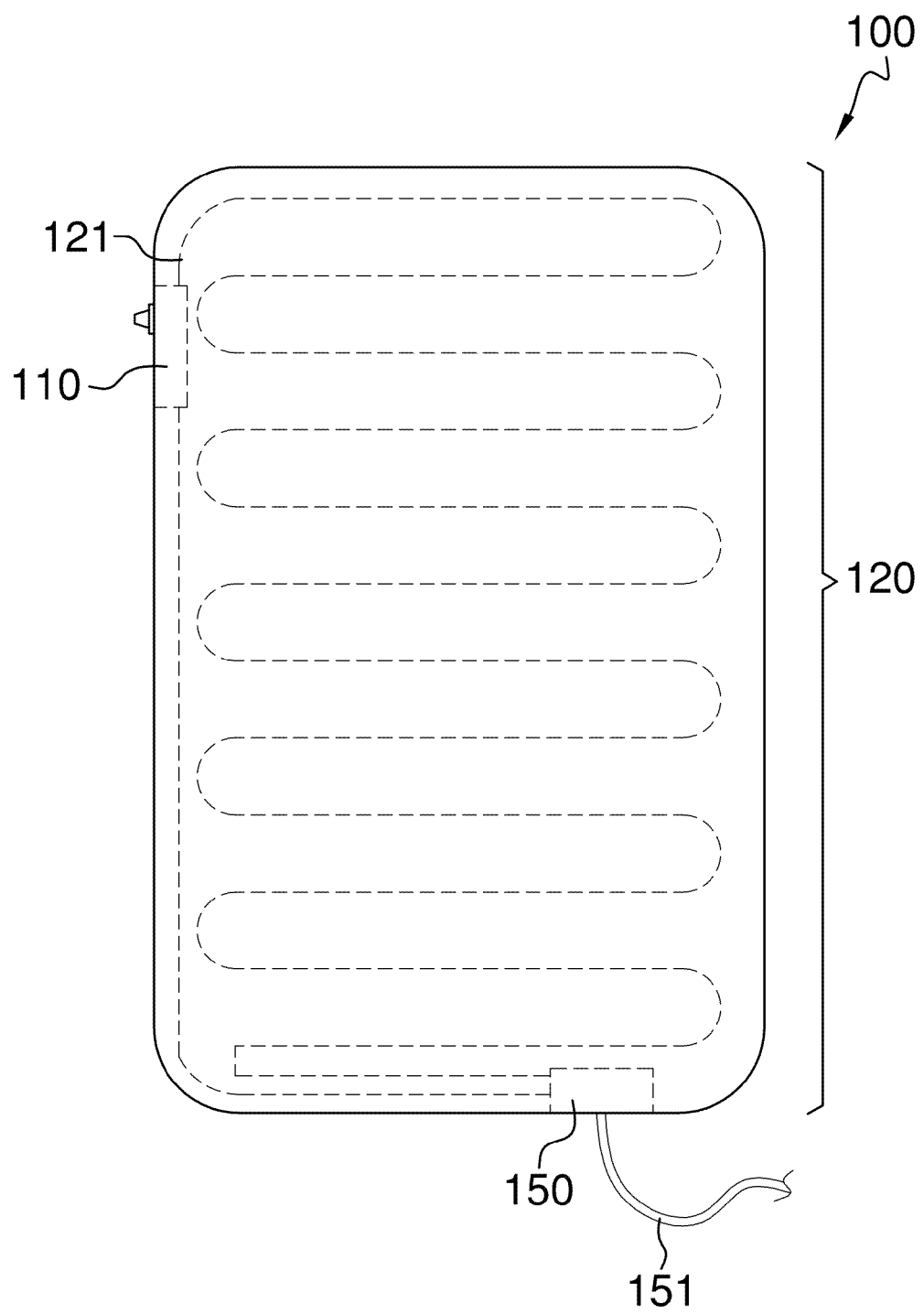
FIG. 3 illustrates a cross-sectional view of the heating element along the first plane.
Figures 4, 5:
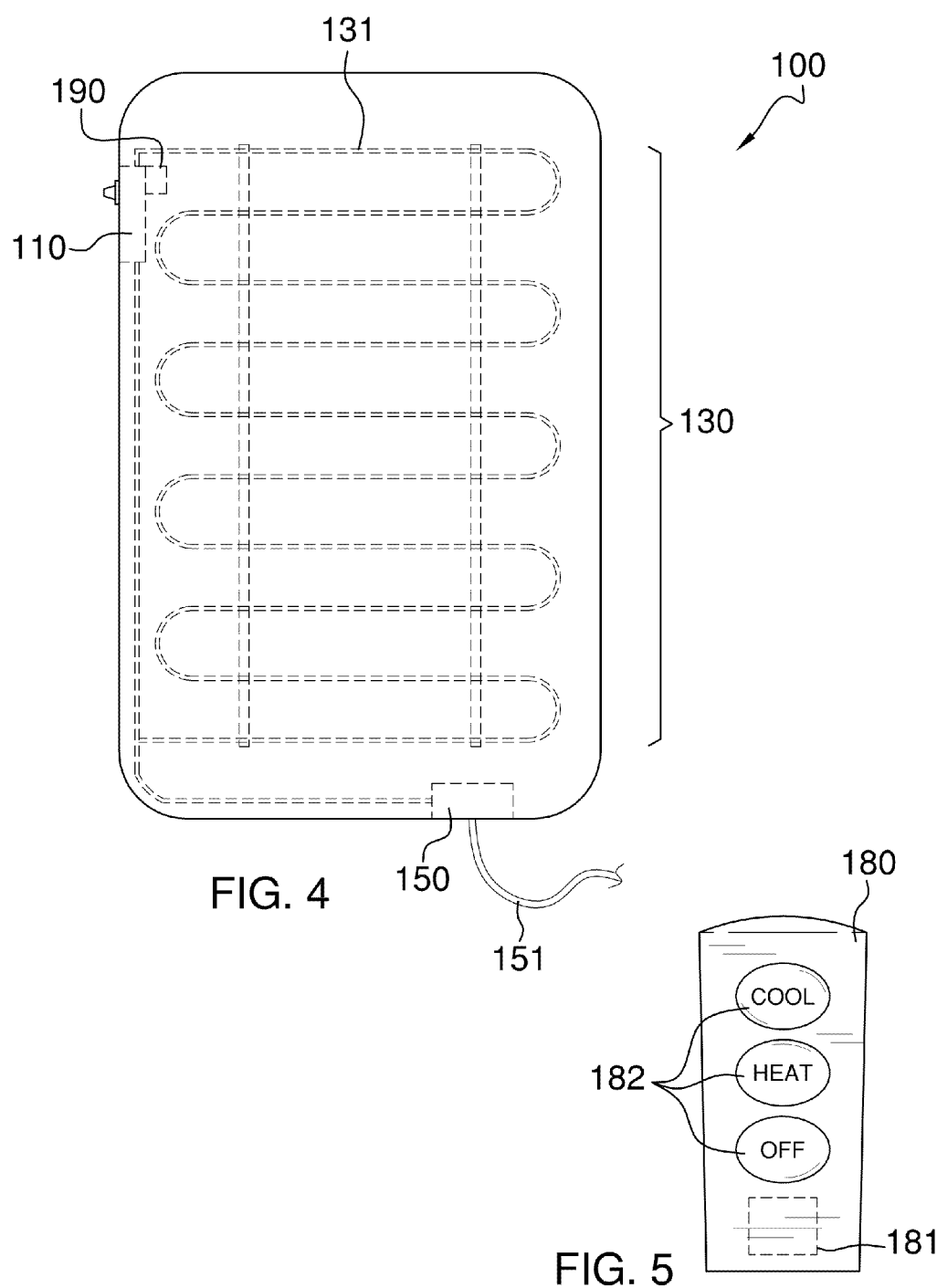
FIG. 4 illustrates a second cross-sectional view of the condenser line along the second plane.
FIG. 5 illustrates a view of a remote control that may be used in conjunction with or in lieu of the control member.

Detailed reference will now be made to the preferred embodiment of the present invention, examples of which are illustrated in FIGS. 1-5. A heating and cooling mattress 100 (hereinafter invention) is further defined with a top surface 101, a first side surface 102, a toe side surface 103.

The first side surface 102 includes a control member 110 that is integrated into the first side surface 102, and which controls operation of a heating member 120 and a cooling member 130. The control member 110 may feature a control knob 111, which can rotate from an OFF position 112 to either a COOL position 113 or a HEAT position 114.

The HEAT position 114 and the COOL position 113 dictate whether the heating member 120 or the cooling member 130 is operating, respectively. The heating member 120 includes a heating element 121 that traverses across an entire surface area of the invention 100. Moreover, the heating element 121 occupies a first plane 125 that is inside of the invention 100. The cooling member 130 includes a refrigeration cycle that includes a condenser line 131 that traverses across the entire surface area of the invention. Moreover, the condenser line 131 occupies a second plane 135.

The first plane 125 is at a lower elevation that when compared to the second plane 135. That being said, heat rises, which necessitates placement of the heating element 121 beneath the condenser line 131. Moreover, the placement of the condenser line 131 is more effective when placed closest to the top surface 101 of the invention 100. It shall be further noted that the first plane 125 and the second plane 135 are generally parallel with one another, and shall be located at a depth underneath the top surface 101 so as not to impact the cushioning of the invention 100 as a bed mattress. Moreover, the second plane 135 shall be located at a second plane depth 140, which is not less than 1 inch beneath the top surface 101 of the invention 100.

The invention 100 includes a powering unit 150, which may be located near the toe side surface 102, and from which a power cord 151 exits the invention 100. The power cord 151 enables electrical power to be provided to the invention 100 in order to power the heating member 120 as well as the cooling member 130. The powering unit 150 is in wired communication with the control member 110, which directs electrical power to either the heating member 120 or the cooling member 130.

The invention 100 may include a remote control 180 that may work in lieu of the control member 110 such that the end user is not required to physically access the control member 110 in order to operate the heating member 120 and the cooling member 130. The remote control 180 is able to communicate wirelessly to the invention 100 via transmitter 181 that is in wired communication with buttons 182 located on the remote control 180. The transmitter 181 communicates wirelessly to a receiver 190 that is in turn wired to the control member 110.

With respect to the above description, it is to be realized that the optimum dimensional relationship for the various components of the invention 100, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 100.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A heating and cooling mattress comprising:
a heating member and a cooling member integrated into the construction of said mattress, and selectively operated in order to heat up or cool down the mattress;
wherein the mattress is further defined with a top surface, a first side surface, and a toe side surface;
wherein the first side surface includes a control member that is integrated into the first side surface, and which controls operation of the heating member and the cooling member;
wherein the control member includes a control knob, which rotate from an OFF position to either a COOL position or a HEAT position;
wherein the HEAT position and the COOL position dictate whether the heating member or the cooling member is operating, respectively;
wherein the heating member includes a heating element that traverses across an entire surface area of the mattress;
wherein the heating element occupies a first plane that is inside of the mattress.

2. The heating and cooling mattress as described in claim 1 wherein the cooling member includes a refrigeration cycle that includes a condenser line that traverses across the entire surface area of the mattress.

3. The heating and cooling mattress as described in claim 2 wherein the condenser line occupies a second plane.

4. The heating and cooling mattress as described in claim 3 wherein the first plane is at a lower elevation that when compared to the second plane.

5. The heating and cooling mattress as described in claim 4 wherein the first plane and the second plane are generally parallel with one another, and shall be located at a depth underneath the top surface.

6. The heating and cooling mattress as described in claim 5 wherein the second plane shall be located at a second plane depth, which is not less than 1 inch beneath the top surface of the mattress.

7. The heating and cooling mattress as described in claim 6 wherein the mattress includes a powering unit, which is located near the toe side surface, and from which a power cord exits in order to provide electrical power to the control member.

8. The heating and cooling mattress as described in claim 7 wherein the powering unit is in wired communication with the control member, which directs electrical power to either the heating member or the cooling member.

9. The heating and cooling mattress as described in claim 8 wherein a remote control works in lieu of the control member in order to operate the heating member and the cooling member; wherein the remote control is able to communicate wirelessly to the control member via transmitter that is in wired communication with buttons located on the remote control; wherein the transmitter communicates wirelessly to a receiver that is in turn wired to the control member.

10. A heating and cooling mattress comprising:
a heating member and a cooling member integrated into the construction of said mattress, and selectively operated in order to heat up or cool down the mattress;
wherein the mattress is further defined with a top surface, a first side surface, and a toe side surface;
wherein the first side surface includes a control member that is integrated into the first side surface, and which controls operation of the heating member and the cooling member;
wherein the control member includes a control knob, which rotate from an OFF position to either a COOL position or a HEAT position;
wherein the HEAT position and the COOL position dictate whether the heating member or the cooling member is operating, respectively;
wherein the heating member includes a heating element that traverses across an entire surface area of the mattress;
wherein the heating element occupies a first plane that is inside of the mattress; wherein the cooling member includes a refrigeration cycle that includes a condenser line that traverses across the entire surface area of the mattress; wherein the condenser line occupies a second plane; wherein the first plane is at a lower elevation that when compared to the second plane; wherein the first plane and the second plane are generally parallel with one another, and shall be located at a depth underneath the top surface.

11. The heating and cooling mattress as described in claim 10 wherein the second plane shall be located at a second plane depth, which is not less than 1 inch beneath the top surface of the mattress; wherein the mattress includes a powering unit, which is located near the toe side surface, and from which a power cord exits in order to provide electrical power to the control member.

12. The heating and cooling mattress as described in claim 11 wherein the powering unit is in wired communication with the control member, which directs electrical power to either the heating member or the cooling member.

13. The heating and cooling mattress as described in claim 12 wherein a remote control works in lieu of the control member in order to operate the heating member and the cooling member; wherein the remote control is able to communicate wirelessly to the control member via transmitter that is in wired communication with buttons located on the remote control; wherein the transmitter communicates wirelessly to a receiver that is in turn wired to the control member.

* * * * *